United States Patent [19]

Naftulin

[11] 4,363,340
[45] Dec. 14, 1982

[54] APPARATUS FOR COLLECTING FLUIDS

[76] Inventor: Henry Naftulin, 8341 N. Kenton Ave., Skokie, Ill. 60076

[21] Appl. No.: 263,474

[22] Filed: May 21, 1981

[51] Int. Cl.³ .................... B65B 31/02; A61M 1/00
[52] U.S. Cl. .................................. 141/51; 128/276; 141/59; 141/114
[58] Field of Search ............... 128/276, 278, 214 R, 128/214 D; 137/205; 141/5, 7, 8, 10, 51, 59, 114, 313–317; 220/85 A, 85 B; 206/522

[56] References Cited
U.S. PATENT DOCUMENTS 4,060,107  11/1977  Naftulin .......................... 141/51 X Primary Examiner—Frederick R. Schmidt
Attorney, Agent, or Firm—Dressler, Goldsmith, Shore, Sutker & Milnamow, Ltd.

[57] ABSTRACT

An apparatus for collecting fluids into flexible containers. The apparatus includes an outer vacuum chamber having a flexible container disposed therein. A split inner chamber is positioned around the flexible container. A bladder means is disposed between the inner chamber and the outer chamber. The bladder means is in communication with the atmosphere so as to cause the bladder means to expand and fill the space between the inner chamber and the outer chamber when the vacuum is applied to the outer chamber.

11 Claims, 9 Drawing Figures

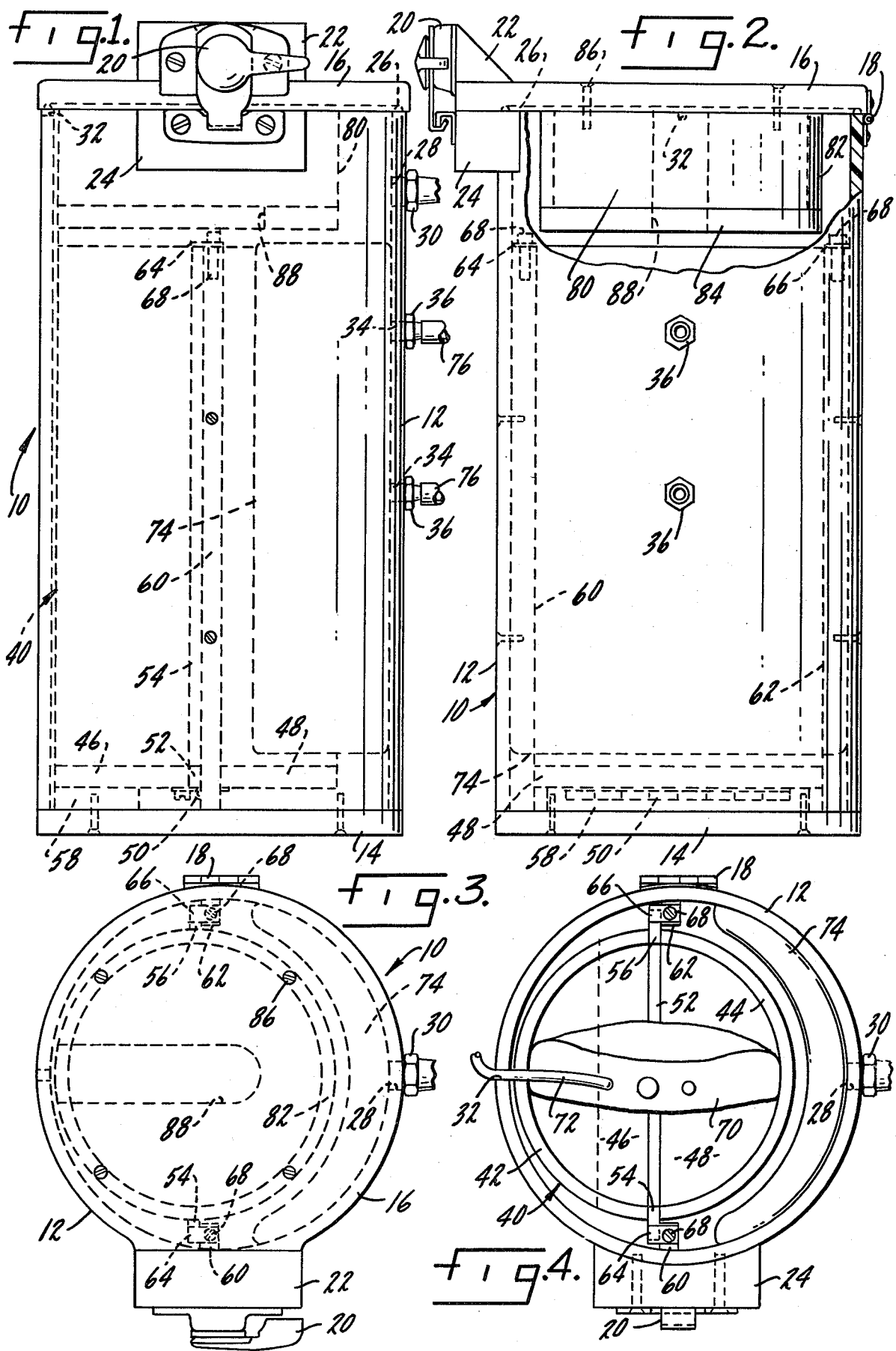

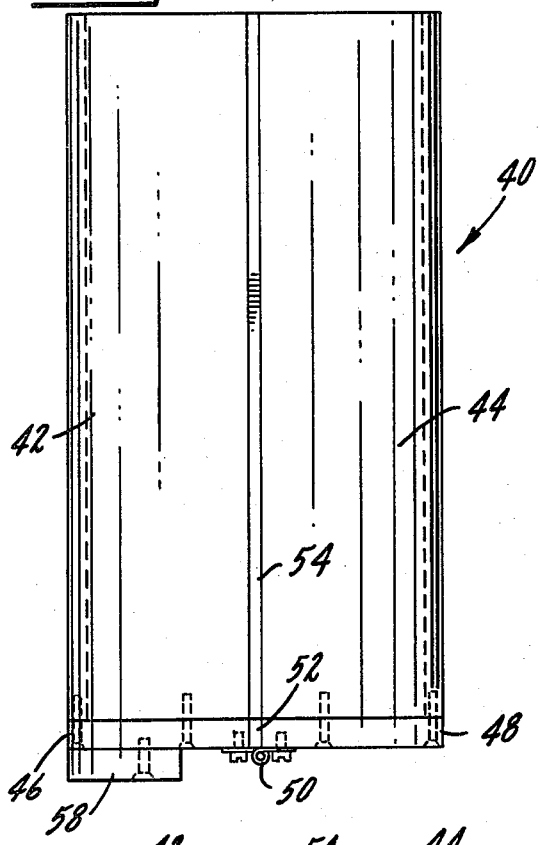
fig.5.
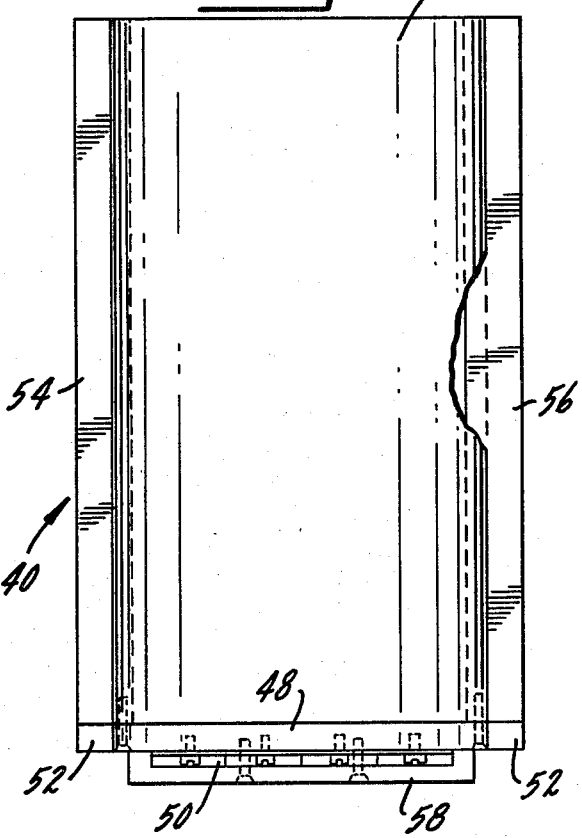
fig.7.
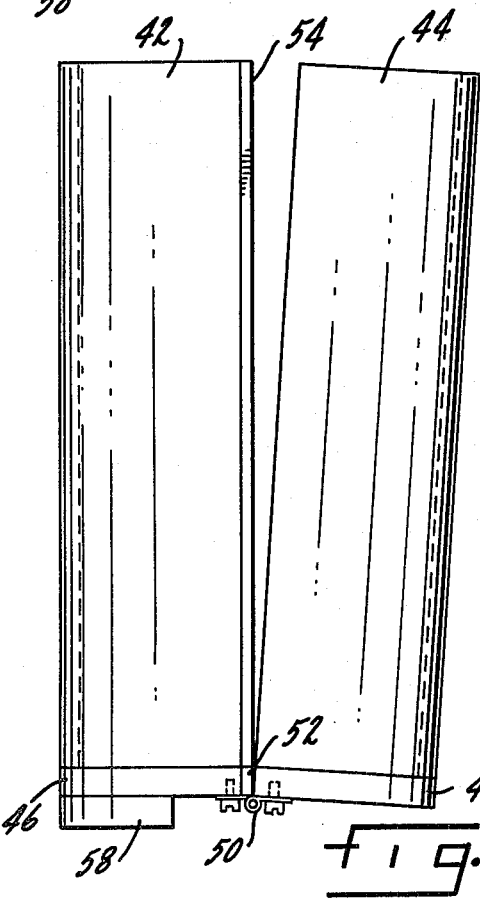
fig.6.
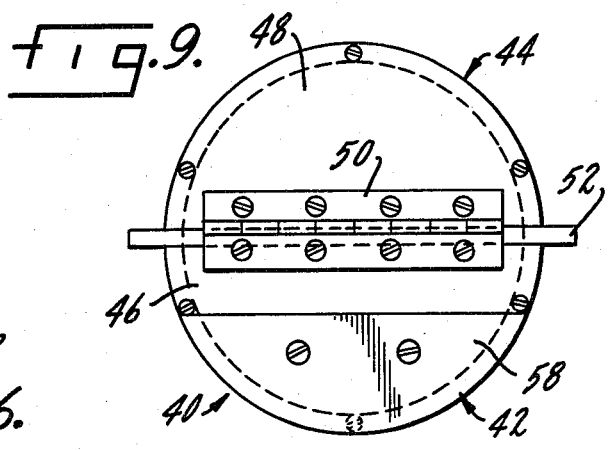
fig.8.
fig.9.

APPARATUS FOR COLLECTING FLUIDS

BACKGROUND OF THE INVENTION

This invention relates to the collection and storage of biological fluids. The invention more particularly relates to an improved apparatus for collecting fluids such as blood, serum, plasma and the like into flexible containers made from plastic, rubberized cloth and the like, which utilizes the unique method as disclosed in U.S. Pat. No. 4,060,107.

In accordance with conventional practices, blood is taken from human donors or animals and stored in sterilized glass bottles and/or flexible containers. Blood is removed from the body of the donor through a phlebotomy needle inserted into a vein, the needle being connected to the storage container by means of flexible tubing. The glass bottles which are used for this purpose require special construction and are therefore relatively costly. In order to reuse these bottles, a careful sterilization process must be effected using special equipment. Further, glass bottles are easily breakable and are not adapted to fit into small or irregular spaces.

In recent years, flexible containers have found wide spread use for the storage of blood. The most commonly used type of flexible containers is manufactured from a plastic material. Collapsible containers, by their very nature, are incapable of being previously evacuated. To solve this problem, the flexible containers have been used in conjunction with blood extracting equipment which includes a vacuum chamber designed to receive the flexible container therein. The vacuum chamber includes means for drawing vacuum therein during the extracting operation. This type of system permits the collection of blood into a flexible container under the influence of a vacuum. However, as the flexible container is being filled, it expands in volume into contact with the sides of the vacuum chamber making it quite difficult to remove the blood filled container from the chamber upon completion of the blood draw. If the vacuum chamber is increased in size to solve the above problem then there is no control of the upper limit of the quantity of blood drawn.

An apparatus for collecting biological fluids is disclosed in U.S.Pat. No. 4,060,107, having the same inventive entity as the present application, which permits the collection of varying quantities of fluid into a flexible container positioned within a vacuum chamber, in a manner which permits the easy withdrawal of the full flexible container from the vacuum chamber. The present invention is an improvement of the apparatus disclosed in U.S. Pat. No. 4,060,107.

SUMMARY OF THE INVENTION

It is a primary object of the present invention to provide an improved apparatus for collecting and storing biological fluids in flexible containers which utilizes the method disclosed in U.S. Pat. No. 4,060,107.

It is a further object of the invention to provide such an apparatus which more accurately defines the limits of expansion of the flexible container.

Another object of the invention is to provide a biological fluid collection apparatus which may be easily cleaned.

A still further object of the invention is to provide a unique means of supporting the inner chamber within the vacuum chamber in a manner which increases the structural integrity of the apparatus.

The apparatus, in accordance with the present invention, includes a rigid outer chamber, having a flexible container disposed therein, for receipt of the collected fluid upon the application of a vacuum within the outer chamber. An inner chamber assembly is positioned within the outer chamber around the flexible container. The inner chamber assembly is disposed within the outer chamber such that an outer surface thereof is in contact with the inner surface of the outer chamber at a point in a tangential vertical plane parallel to a vertical plane which splits the inner chamber into two segments. The segment which contacts the outer chamber is rigidly secured in place and pivotally secured to the other segment in a manner which permits movement of the other segment between an open position and a closed position. A bladder is disposed within the outer chamber between the inner chamber and the outer chamber adjacent to the segment of the inner chamber not in contact with the outer chamber. The interior of the bladder is in communication with the atmosphere so as to cause the bladder to expand and fill the space between the inner chamber and the outer chamber upon the application of a vacuum to the outer chamber so as to exert a pressure on the movable inner chamber segment and thereby move the segment to its closed position. A retainer member depends downward from the underside of a lid member which closes off the upper end of the outer chamber. The retainer member is effective to limit the expansion of the flexible container.

BRIEF DESCRIPTION OF THE DRAWINGS

These and other objects and advantages of the invention will become apparent from the following description when taken in connection with the accompanying drawings. In the drawings, wherein like reference numbers have been used to indicate like parts throughout:

FIG. 1 is a front elevational view of the apparatus in accordance with the present invention with the flexible container removed;

FIG. 2 is a side elevational view of the apparatus shown in FIG. 1 taken from the right side;

FIG. 3 is a top plan view of the apparatus as shown in FIG. 1;

FIG. 4 is a top plan view of the apparatus as shown in FIG. 1 with the lid member removed and the flexible container positioned therein;

FIG. 5 is a front elevational view of the inner chamber assembly shown in its closed position;

FIG. 6 is a front elevational view of the inner chamber assembly shown in its open position;

FIG. 7 is a side elevational view of the inner chamber assembly as shown in FIG. 5;

FIG. 8 is a top plan view of the inner chamber assembly as shown in FIG. 7; and

FIG. 9 is a bottom plan view of the inner chamber assembly as shown in FIG. 7.

DESCRIPTION OF A PREFERRED EMBODIMENT

Referring now to the drawings and in particular to FIGS. 1-4, there is shown an apparatus for collecting and storing biological fluids in accordance with and embodying the principles of the present invention, the apparatus generally being designated by the numeral 10. Apparatus 10 includes an outer chamber 12 of rigid construction and fabricated from a suitable material possessing the necessary strength and rigidity. Examples of materials are glass, plastics, metals and the like. A transparent plastic material is a preferred material of construction for the outer chamber 12 so as to permit visual examination of its interior.

In the embodiment of the invention as shown in the drawing, chamber 12 is formed from an upright cylinder which is closed at its bottom end by a bottom portion 14 and open at its upper end. A lid member 16 is pivotally secured to the other wall of chamber 12 adjacent to its upper end through hinge member 18. Lid member 16 pivots between a closed position, as shown in FIGS. 1 and 2, and an open position which permits complete access to the interior of chamber 12. A suitable locking assembly 20 is provided to retain lid member 16 in its closed position. Assembly 20 is secured to a structural member 22, which in turn is secured to the upper surface of lid member 16 adjacent the outer edge thereof in opposing relationship to hinge member 18, and to structural member 24, which in turn is secured to the outer surface of the upper end of chamber 12 immediately below the upper edge thereof. A sealing o-ring 26 is provided in the undersurface of lid member 16 in sealing relationship with the upper edge of chamber 12 when lid member is in its closed position.

An opening 28 is provided through an upper portion of chamber 12 for receipt of a tapered fitting 30 therein. Fitting 30 extends outwardly from chamber 12 and is adapted to be connected to a vacuum line (not shown) to draw a vacuum within chamber 12. An opening 32 is integrally formed at the upper periphery of chamber 12 to permit a fluid collection line to pass therethrough in a manner which will hereinafter become more apparent. A pair of openings 34 are provided through intermediate portions of chamber 12 for receipt of fittings 36 therethrough. Fittings 36 extend outwardly from chamber 12 and are adapted to be connected to bladder lines for reasons which will hereinafter become more apparent.

An inner chamber assembly 40 is positioned within chamber 12. Referring to FIGS. 5–9, inner chamber assembly 40 is constructed of two opposing cylindrical segment members 42 and 44, having bottom portions 46 and 48 respectively which are pivotally secured together by a hinge member 50. Segments 42 and 44 are formed by cutting a cylindrical tube longitudinally in half and therefore are slightly less than half circles in horizontal cross section owing to the thickness of the cutting tool. A bottom spacer member 52 is secured to bottom portion 46 to compensate for the material removed by the cutting tool. Spacer member 52 is preferably of the same thickness as bottom portion 46. A pair of vertically extending spacer members 54 and 56 are secured to the respective edges of segment 42 along the entire length thereof. Spacer members 54 and 56 extend outwardly from a respective inner surface of segment 42 and terminate a short distance beyond the outer surface of segment 42. Spacer members 54 and 56 serve the dual purpose of compensating for the material removed by the cutting tool and to provide outwardly extending vertical flanges which are used to retain inner chamber assembly 40 within outer chamber 12. A spacer block 58 is secured to the underside of bottom portion 48 to elevate assembly 40 and thereby permit segment 44 to pivot between a closed position in contact with members 54 and 56, as seen in FIG. 5, and an open position spaced from members 54 and 56, as seen in FIG. 6.

Referring once again to FIGS. 1–4, inner chamber assembly 40 is positioned within outer chamber 12 such that segment 42 is in contact with the inner surface of chamber 12 and block 58 is resting on bottom portion 14. Assembly 40 is further positioned such that the vertical plane passing through members 54 and 56 is in opposing relationship to fittings 36. A pair of vertically extending hold down rails 60 and 62 are secured to the inner surface of chamber 12 in diametrically opposing relationship so as to contact members 54 and 56 and thereby retain inner chamber assembly 40 rigidly in place within chamber 12. Rails 60 and 62 extend upward to the same elevation as members 54 and 56. Hold down straps 64 and 66 extend respectively across member 54 and rail 60 and member 56 and rail 62. Hold down members 64 and 66 are removably secured to rails 60 and 62 by removable fasteners, such as screws 68, which extend through the members 64 and 66 respectively into members 54 and 56.

Referring to FIG. 4, a fluid collecting flexible container or bag 70 is positioned within inner chamber assembly 40. Container 70 is of conventional construction and may be made from many flexible materials well known in the art, the most commonly used type being manufactured from a plastic material such as a polyvinyl chloride resin base material. Container 70 includes a fluid collection line 72 having one end in communication with the interior of container 70 and the other end extending through opening 32 for receipt of the collected fluid thereinto.

As seen in FIGS. 1–4, a flexible bladder member 74 is positioned within outer chamber 12 adjacent segment 44. Bladder 74 extends substantially around the entire periphery of segment 44 and the entire height thereof. Bladder 74 includes a pair of bladder lines 76 having one end in communication with the interior of bladder 74 and another end passing through a corresponding fitting 36 in chamber 12 for communication with the atmosphere. The interior of bladder 74 is thus in communication with the atmosphere through lines 76.

Referring to FIGS. 1–3, a retainer member 80 is secured to the underside of lid member 16. Retainer member 80 includes an upright cylindrical portion 82 and a bottom portion 84 closing off the lower end of portion 82. Portion 82 is approximately the same diameter as inner chamber assembly 40. The upper end of portion 82 is secured to the underside of lid member 80 through removable fasteners 86. Retainer member 80 extends downwardly into chamber 2, when lid member 16 is in its closed position, a distance such that portion 84 is at an elevation just above the upper edges of inner chamber assembly 40. A cutout portion 88 is formed in retainer member 80, as best seen in FIG. 3, so to permit line 72 to pass therethrough and out opening 32.

The operation of the above described preferred embodiment of the invention will now be described as used to collect blood from an animal such as a fetal calf. An empty flexible container 70 is positioned within inner chamber assembly 40, which is in an open position as shown in FIG. 6. The fluid collection line 72 is extended through cutout portion 88 and opening 32 and the lid member 16 is lowered to its closed position and locked in place with lock member 20. The fluid collection line 72 is then clamped off outside of outer chamber 12. A vacuum is drawn in outer chamber 12 through a vacuum line (not shown) which is connected to fitting 30 at one end and a source of vacuum such as a vacuum pump (not shown) at the other end. As the vacuum is drawn in chamber 12, the bladder member 74 is caused to expand due to the fact that it is vented to atmosphere through lines 76. The resultant expansion of bladder 74 exerts pressure on segment 44 of inner chamber assembly, moving it into contact with members 54 and 56 to attain the closed position of assembly 40, as seen in FIG. 5. Apparatus 10 is now in the condition shown in FIGS. 1-4 and ready for use to collect blood into container 70.

To collect blood from the animal, a phlebotomy is performed in the animal with the terminal end of collection line 72. Upon removal of the clamp from line 72, the negative pressure, created by the vacuum in outer chamber 12, against the walls of container 70 cause it to expand and blood to be drawn thereinto. The rate of blood withdrawal may be controlled by the regulation of the degree of vacuum drawn in outer chamber 12. An increase in the vacuum in chamber 12 will increase the flow rate of blood into container 70.

Apparatus 10 utilizes the flexibility and expandibility of container 70 as the blood is being collected. Container 70 fills and expands to the confines of inner chamber assembly 40 as defined at its upper end by retainer member 80. The amount of blood which is collected depends on the side of inner chamber assembly 40, the position of retainer member 80, and the degree of vacuum within outer chamber 12. By changing or adjusting these variables, the amount of blood drawn can be controlled.

After the desired amount of blood has been collected, the collection line 72 is again clamped off, the vacuum source is shut off, and the outer chamber 12 is vented to atmosphere by apending lid member 16. The venting of outer chamber 12 causes the bladder 74 to deflate, which in turn causes the inner chamber assembly 40 to split apart into its open position. The container 70, full with blood, which would otherwise be difficult to remove, may be easily removed from the inner chamber assembly 40 because it is no longer exerting pressure against the walls of segments 42 and 44.

The hereinabove described apparatus 10 provides many improvements over the blood collecting apparatus disclosed in U.S. Pat. No. 4,060,107. The addition of the retainer member 80 more positively defines the total expansion limits of the container 70. This permits more accurate control of the amount of blood drawn from an animal or human. As mentioned hereinabove, the retainer member 80 is removably secured to lid member 16. The present invention contemplates the interchangeability of members 80 of different sizes to change the expansion limits of the container 70. Further, it is within the teachings of the invention to even provide a single member 80 whose extension into inner chamber 40 can be selectively controlled. This could be attained by securing member 80 to lid member 16 in a manner which permits vertical adjustment at the length of member 80.

The inner chamber assembly 40 is removably secured within chamber 12 in a manner which assures reliable operation and permits easy removal thereof for cleaning. The inner chamber assembly 40 is secured in a fixed position within outer chamber 12 so as to make sure that the bladder member 74 always contacts segment 44 dead center and thereby minimizes the torque forces applied to the assembly 40. Further, the inner chamber assembly 40 is easily removed by loosening fasteners 68 and rotating hold down straps 64 and 66 ninety degrees, and thereby allowing the entire assembly to be vertically lifted from chamber 12. It should further be noted that the provision of multiple bladder lines 76 which extend through openings 34 in chamber 12 serve to retain the bladder more positively in place.

The provision of locking member 20 to retain lid member 16 in its closed position is particularly advantageous if the apparatus 10 is utilized to defibrinate blood in a manner as disclosed in U.S. Pat. No. 4,129,131. By locking lid member 16 in its closed position, if the vacuum within chamber 12 is lost while the chamber is shaking during the defibrination procedure, the lid member will not fly open and thereby disrupt the procedure and probably damage the apparatus 10.

This invention is not to be limited by the embodiment shown in the drawings and described in the description which are given by way of example and not of limitation, but only in accordance with the spirit and scope of the appended claims.

What is claimed is:

1. Apparatus for collecting and storing biological fluids in a flexible container, comprising:
   (a) a rigid outer chamber having a fluid inlet opening and a vacuum port, said flexible container being disposed within said outer chamber in communication with said fluid inlet opening for receipt of fluid therein upon creation of a vacuum within said outer chamber through said vacuum port;
   (b) inner chamber means disposed within said outer chamber for receipt of said flexible container therein, said inner chamber being split into at least two segments which are movable between a closed position and an open position, said inner chamber means defining a smaller volume when in its closed position than when in its open position;
   (c) bladder means disposed within said outer chamber between said inner chamber means and said outer chamber, the interior of said bladder means being in communication through an opening in said outer chamber with the atmosphere so as to cause said bladder means to expand and fill a space between said inner chamber and said outer chamber upon the application of a vacuum to said outer chamber so as to exert a pressure on said inner chamber sections and thereby move said sections toward one another into its closed position; and
   (d) retainer means depending downward from the underside of a lid member, said lid member being pivotally mounted to said outer chamber adjacent to the upper end thereof so as to close off the upper end of said outer chamber when in its closed position, said retainer means extending downward towards said inner chamber means and being effective to limit the expansion of said flexible container.

2. The invention as defined in claim 1 wherein said retainer means extends downward to a position a short distance above the upper edges of said inner chamber means.

3. The invention as defined in claim 2 wherein said retainer means includes a slot formed therein so as to permit a fluid inlet line associated with said flexible container to pass therethrough.

4. The invention as defined in claim 1 wherein said retainer means is removably secured to said lid member.

5. The invention as defined in claim 1 wherein said retainer means includes a cylindrical portion having a diameter substantially equal to the diameter of said inner chamber means and a bottom portion closing off the lower end of said cylindrical portion.

6. The invention as defined in claim 1 wherein a locking means is provided to lock said lid member in its closed position.

7. Apparatus for collecting and storing biological fluids, comprising:
(a) a rigid cylindrical outer chamber having a closed bottom end and a pivotally mounted lid member closing off the upper end, said outer chamber having a fluid inlet opening and a vacuum port;
(b) a cylindrical inner chamber means being formed from two segments of a closed bottom cylinder which are pivotally connected together at their bottoms so as to permit movement between an open position and a closed position, said inner chamber means being of a diameter less than the diameter of said outer chamber, said inner chamber means being disposed within said outer chamber such that an outer surface thereof is in contact with the inner surface of said outer chamber at a point in a tangential vertical plane parallel to the vertical plan separating said segments, said segment which contacts said outer chamber having a spacer member secured to the bottom surface thereof so as to raise said inner chamber means above the bottom of said outer chamber and permit movement thereof between its open and closed positions;
(c) a flexible container disposed within said inner chamber means in communication with said fluid inlet for receipt of fluid therein upon the application of a vacuum within said outer chamber through said vacuum port; and
(d) bladder means disposed within said outer chamber between said inner chamber means and said outer chamber adjacent the segment of said inner chamber means not in contact with said outer chamber, the interior of said bladder means being in communication through an opening in said outer chamber with the atmosphere so as to cause said bladder means to expand and fill the space between said inner chamber and said outer chamber upon the application of a vacuum to said outer chamber and thereby exert a pressure on said inner chamber segments and move said segments towards one another into their closed position.

8. The invention as defined in claim 7 wherein said segment of said inner chamber means which contacts said outer chamber is rigidly held in place within said outer chamber.

9. The invention as defined in claim 8 wherein said inner chamber means releasably secured to said outer chamber.

10. The invention as defined in claim 9 wherein said outer chamber includes a pair of diametrically opposed rail means secured to the inner surface of said outer chamber and said segment of said inner chamber means which contacts said outer chamber includes a pair of spacer means which contact said rail means and thereby retain said inner chamber means against said outer chamber.

11. The invention as defined in claim 10 wherein hold down means are provided across said rail means and said spacer means.

* * * * *